US012589186B2

(12) United States Patent
Naso et al.

(10) Patent No.: US 12,589,186 B2
(45) **Date of Patent: \*Mar. 31, 2026**

(54) METHOD FOR INACTIVATING XENOANTIGENS IN BIOLOGICAL TISSUES

(71) Applicant: BIOCOMPATIBILITY INNOVATION S.R.L., Padua (IT)

(72) Inventors: Filippo Naso, Ospedaletto Euganeo (IT); Alessandro Gandaglia, Rubano (IT)

(73) Assignee: BIOCOMPATIBILITY INNOVATION S.R.L., Padua (IT)

( \* ) Notice: Subject to any disclaimer, the term of this patent is extended or adjusted under 35 U.S.C. 154(b) by 285 days.

This patent is subject to a terminal disclaimer.

(21) Appl. No.: 15/779,953

(22) PCT Filed: Nov. 25, 2016

(86) PCT No.: PCT/EP2016/078898
§ 371 (c)(1),
(2) Date: May 30, 2018

(87) PCT Pub. No.: WO2017/093147
PCT Pub. Date: Jun. 8, 2017

(65) Prior Publication Data
US 2018/0353647 A1 Dec. 13, 2018

(30) Foreign Application Priority Data
Nov. 30, 2015 (IT) ......................... 102015000078236

(51) Int. Cl.
*A61L 27/36* (2006.01)
(52) U.S. Cl.
CPC ....... *A61L 27/3687* (2013.01); *A61L 27/3625* (2013.01); *A61L 2430/20* (2013.01); *A61L 2430/40* (2013.01)
(58) Field of Classification Search
CPC ... A61L 27/3687; A61L 27/36; A61L 2430/40
See application file for complete search history.

(56) References Cited

U.S. PATENT DOCUMENTS

| | | | | |
|---|---|---|---|---|
| 9,795,573 | B2 * | 10/2017 | Vyavahare et al. .... | A01N 43/04 |
| | | | | 31/15 |
| 11,951,078 | B2 * | 4/2024 | Naso et al. ............ | A61K 31/05 |
| 2014/0018909 | A1 * | 1/2014 | Simionescu et al. ........................ | |
| | | | | A61K 31/7034 |
| | | | | 623/1.49 |
| 2015/0087611 | A1 * | 3/2015 | Vyavahare et al. .. | C12N 5/0652 |
| | | | | 514/39 |

FOREIGN PATENT DOCUMENTS

| | | |
|---|---|---|
| EP | 2 626 701 | 8/2013 |
| EP | 2 626 701 A1 | 8/2013 |
| WO | WO2004047620 A2 * | 6/2004 |
| WO | WO2007133479 A2 * | 11/2007 |

OTHER PUBLICATIONS

Naso et al. "First quantification of alpha-Gal epitope in current glutaraldehyde-fixed heart valve bioprostheses", Xenotransplantation, 2013: 20: 252-261. (Year: 2013).*
Combrinck et al. "Morphology and Histochemistry of the Glandular Trichomes of Lippia scaberrima (Verbenaceae)", Annals of Botany 99: 1111-1119, 2007. (Year: 2007).*
Somers et al. "Non-Cytotoxic Crosslinkers for Heart Valve Tissue Engineering", The Journal of Heart Valve Disease, Jan. 2015, 24:92-100. (Year: 2015).*
Goncalves et al. (2005) "Decellularization of Bovine Pericardium for Tissue- Engineering by Targeted Removal of Xenoantigens" J Heart Valve Dis, vol. 14, No. 2, pp. 212-217. (Year: 2005).*
Robbins et al. (2003) "Phenolic acids in foods: an overview of analytical methodology" Journal of agricultural and food chemistry, 51(10), 2866-2887. (Year: 2003).*
Hayat, M.A. (1981) "Factors Affecting the Quality of Fixation" Fixation for electron microscopy, published by Academic Press, New York, pp. 9-63. (Year: 1981).*
Naso et al. (2011) "First quantitative assay of alpha-Gal in soft tissues: presence and distribution of the epitope before and after cell removal from xenogeneic heart valves" Acta biomaterialia, 7(4), 1728-1734. (Year: 2011).*
International Search Report and Written Opinion of the International Searching Authority for International Patent Application No. PCT/EP2016/078898 mailed Feb. 17, 2017, 9 pages.
European Examination Report for European Patent Application No. 16801773.9 mailed Aug. 6, 2019, 6 pages.
Berryman, M. et al., "Effects of tannic acid on antigenicity and membrane contrast in ultrastructural Immunocytochemistry", Journal of Histochemistry and Cytochemistry, 40(6): 845-857 (Jun. 1992).
Naso, F. et al., "First quantification of alpha-Gal epitope in current glutaraldehyde-fixed heart valve bioprostheses", Xenotransplantation, 20(4): 252-261 (2013).
Galili, Uri, The α-gal epitope and the anti-Gal antibody in xenotransplantation and in cancer immunotherapy, Immunology and Cell Biology, 2005, Australasian Society for Immunology, Inc., pp. 674-686.

(Continued)

*Primary Examiner* — James Joseph Graber
(74) *Attorney, Agent, or Firm* — Merchant & Gould P.C.

(57) ABSTRACT

A method is for inactivating xenoantigens in biological tissues, particularly in tissues that can be used to manufacture bioprosthetic substitutes and/or in bioprosthetic substitutes that are already prepared and intended for human or veterinary clinical use. The method entails the following steps: providing a solution based on phenolic compounds, polyphenolic compounds or derivatives thereof, for the inactivation of at least part of the xenogeneic epitopes from such tissues; incubating the samples to be treated in the various solutions based on phenols/polyphenols in controlled conditions; and subjecting the treated tissues to a series of washes.

7 Claims, 2 Drawing Sheets

(56) References Cited

OTHER PUBLICATIONS

Macher, Bruce A. et al., The Galα1,3Galβ1,4GIcNAc-R (α-Gal) epitope: a carbohydrate of unique evolution and clinical relevance, National Institutes of Health, NIH Public Access, Biochim Biophys Acta., Author manuscript, PMC 2009, Feb. 1, pp. 1-25.

Naso, F., et al., First quantitative assay of alpha-Gal in soft tissues: Presence and distribution of the epitope before and after cell removal from xenogeneic heart valves, Elsevier, Acta Biomaterialia 7, 2011, pp. 1728-1734.

* cited by examiner

METHOD FOR INACTIVATING XENOANTIGENS IN BIOLOGICAL TISSUES

This application is a National Stage Application of PCT/EP2016/078898, filed 25 Nov. 2016, which claims benefit of Serial No. 102015000078236, filed 30 Nov. 2015 in Italy and which applications are incorporated herein by reference. To the extent appropriate, a claim of priority is made to each of the above-disclosed applications.

BACKGROUND OF THE INVENTION

The present invention relates to a method for inactivating xenoantigens in biological tissues, in particular for inactivating xenoantigens in tissues that can be used to manufacture bioprosthetic substitutes, intended for use in the human or veterinary clinical field.

In particular the invention relates to a method for ensuring the inactivation of xenoantigens in connective tissues that are native and/or fixed, heterologous or homologous, in particular of the alpha-Gal epitope, in particular in cardiovascular tissues through the use of biological activities identified in phenolic compounds, polyphenolic compounds and derivatives thereof.

The production of bioprosthetic substitutes is currently a market undergoing major expansion. The clinical improvement of surgical procedures, the decrease in post-surgical complications, the development and management of new immune-modulating medicines, combined with a deeper knowledge of the interaction mechanisms between graft and host, all contribute to facilitating where possible the use of biological prostheses constituted by animal or homologous tissue. In this sense, one sector that is representative but non-limiting is the cardiovascular sector, especially in terms of the social and health impact that the established practice of cardiac valve replacement can cause.

Biomedical technology is capable of developing and surgically applying for replacement purpose, valve prostheses that can imitate the opening and closing function of dysfunctional native valves.

The ideal valve prostheses should be capable of allowing a trans-valve flow that can overlap that of the analog original, healthy valve, ensure a long lifetime and not generate hemolytic or thrombogenic effects.

The valve substitutes that are most often used are biological prostheses derived from xenogeneic tissues, in particular from pig valves or valves produced with bovine or equine pericardium.

Such valve prostheses and substitutes have the disadvantage that they encounter degenerative processes of calcific dystrophy and/or deterioration with breakage of the cusps, exhibiting a greater sensitivity toward the onset of endocardial infections. For the purpose of improving their mechanical characteristics, decreasing their intrinsic antigenicity, and enabling their preservation, they are usually treated with cross-linking/sterilizing chemical agents such as, for the purposes of non-exclusive example, glutaraldehyde. In addition they can be subjected to treatments according to decalcification or detoxification protocols.

The term "xenogeneic tissue" means a tissue that belongs to an organism of a species other than human; such materials have specific surface antigens that are tolerable inside the species of origin, but which are incompatible when implanted in humans where, if not adequately treated, they are capable of triggering the activation of the complement cascade with platelet aggregation, producing a situation similar to that occurring in the case of a blood group incompatibility.

Such phenomenon is known by the term "hyperacute rejection". The principal cause of the onset of such mechanism is the presence of the alpha-Gal xenoantigen. This epitope is a di-galactoside (galactose-alpha1,3-galactose) present on membrane glycoproteins and glycolipids (primarily of endothelial cells), as well as on different cell types such as monocytes, granulocytes and red blood cells and in important tissue districts such as the myocardial and bone regions. Such crucial antigen is constitutively expressed in all mammals, except in the higher primates and humans.

The human body, from birth, expresses antibodies directed against such epitope as a result of continuous stimulation by the intestinal bacterial flora.

Today, the biocompatibility of the xenogeneic tissues intended for use in manufacturing bioprostheses is obtained by treating with the aforementioned glutaraldehyde.

Despite such procedure, the alpha-Gal epitope has been shown to remain responsive in currently marketed valve substitutes, causing, after the implant, an increase in the anti-alpha-Gal antibodies circulating both in pediatric patients and in adults.

Furthermore, the antigen-antibody complex that is formed appears to be directly involved in promoting the deposition of calcium salts, favoring the formation of episodes of calcific dystrophy of the valve.

SUMMARY OF THE INVENTION

The aim of the present invention is to provide a method for inactivating xenoantigens in biological tissues that is capable of overcoming the limitations of conventional treatments.

Within this aim, an object of the invention is to provide a method that can be applied to connective tissues that are native and/or fixed, heterologous or homologous, which can be used for manufacturing bioprosthetic substitutes, for use in the human or veterinary clinical field.

A further object of the invention is to provide a method for inactivating xenoantigens in biological tissues that is adapted to ensure the inactivation of the alpha-Gal epitope in cardiovascular tissues.

Another object of the invention is to provide a method for inactivating xenoantigens in biological tissues with which to inactivate the above mentioned epitopes thus ensuring an effective treatment that can be applied to the various different types of bioprosthetic substitutes currently on the market.

Another object of the invention is to provide a method that does not favor, after an implant, an increase in circulating anti-alpha-Gal antibodies.

Another object of the invention is to provide a method that does not promote the deposition of calcium salts, therefore limiting the formation of episodes of calcific dystrophy of the valve.

Another object of the invention is to provide a method that can be carried out with conventional devices and machines.

This aim and these and other objects which will become better evident hereinafter are achieved by a method for inactivating xenoantigens in biological tissues, particularly in tissues that can be used to manufacture bioprosthetic substitutes and/or in bioprosthetic substitutes that are already prepared and intended for human or veterinary clinical use, characterized in that it entails the following steps:

providing a solution based on phenolic compounds, poly-
phenolic compounds or derivatives thereof, for the
inactivation of at least part of the xenogeneic epitopes
from said tissues;
incubating the samples to be treated in the various solu-
tions based on phenols/polyphenols in controlled con-
ditions;
subjecting the treated tissues to a series of washes.

The invention also relates to a connective tissue obtained
with a method for inactivating xenoantigens in biological
tissues according to the invention as described above, char-
acterized in that it has at least some of the antigen compo-
nent in inactive form.

The invention also relates to a use of connective tissue,
obtained with a method for inactivating xenoantigens in
biological tissues according to the invention as described
above, for the manufacture of bioprosthetic substitutes and/
or parts of bioprosthetic substitutes that are already pre-
pared, for use in the human or veterinary clinical field.

The invention also relates to a kit for carrying out a
method for inactivating xenoantigens in biological tissues
according to the invention as described above, characterized
in that it comprises at least:

one or more containers containing the buffer in which the
most suitable dose of phenolic compounds, polyphe-
nolic compounds or derivatives thereof is to be dis-
solved;
one or more containers containing the dose of phenolic
compounds, polyphenolic compounds or derivatives
thereof in powder form to be combined with the buffer;
one or more containers containing the washing buffers;
an instruction booklet containing the description of the
timings and modes of application of the procedure.

BRIEF DESCRIPTION OF THE DRAWINGS

Further characteristics and advantages of the invention
will become better apparent from the detailed description
that follows of a preferred, but not exclusive, embodiment,
of the method for inactivating xenoantigens in biological
tissues according to the invention. In the accompanying
drawings.

DEFINITIONS

Detailed Description of the Preferred Embodiments

Figure 1:
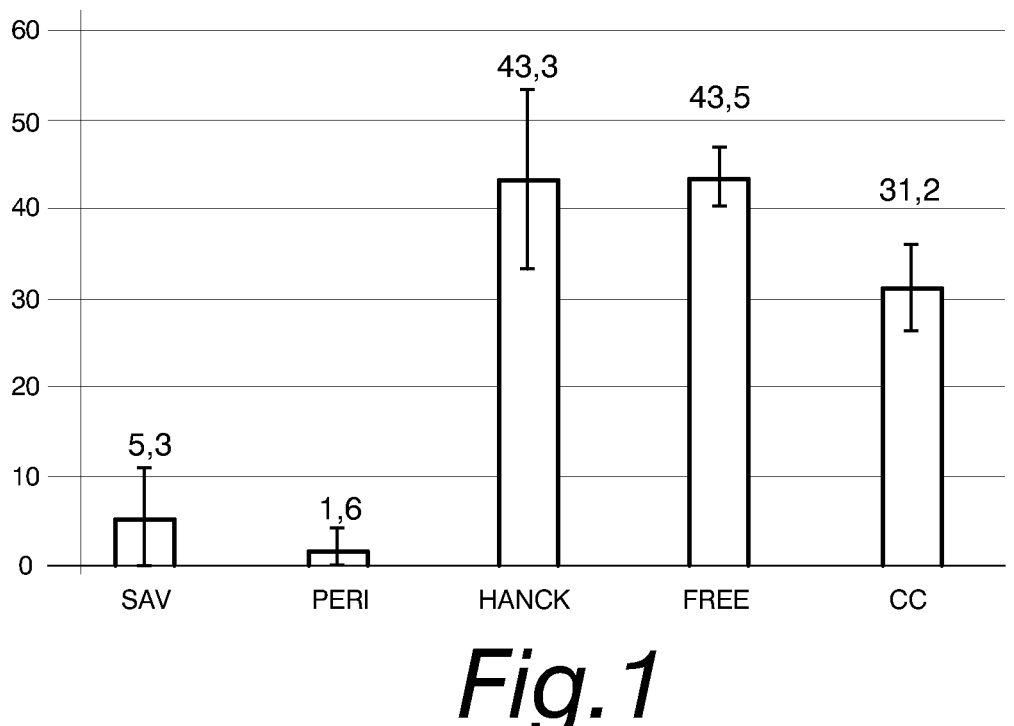
FIG. 1 is a view of the results, in percentages, of the
application of a method according to the invention in a first
variation of application thereof.

The term "phenolic compounds" refers to molecules
characterized, at least in part thereof, by the presence of an
aromatic nucleus (benzene ring) bound to one or more
hydroxyl functional groups. The above mentioned com-
pounds include, for the purposes of non-exclusive example:
simple phenols (molecules with a single benzene ring and
containing only hydroxyl groups as substituents, e.g. phenol
and hydroquinone), phenolic aldehydes (containing both the phenolic group and the aldehyde group, e.g. aldeide van-
illica), phenolic acids (e.g. cinnamic acids), phenylamines
(amphoteric molecules containing a weakly acidic group and
a strongly basic group, e.g. phenylalanine), phenol com-
pounds (the phenolic ring is bound to another benzene ring
or to other heterocyclic compounds that have hydroxyl/
lactone/ketone functional groups, e.g. coumarins and xan-
thones), flavonoids (made up of two benzene rings con-
nected by a chain with three carbon atoms that constitutes an
oxygenated heterocyclic ring, e.g. catechins, flavonons, fla-
vones, chalcones, flavanonols, flavanols, leucoanthocyani-
din, anthocyanidin), phenylpropanoids (characterized by the
presence of an aromatic ring with an aliphatic side chain
with three carbon atoms, es. hydroxycinnamic acids) and
tannins. In the present invention the terms "phenols" and
"polyphenols" can have the same meaning, and can be used
together or to substitute for each other for the set aims.

The term "xenoantigen" refers to molecules of animal
origin that can be recognized by the immune and can induce
an antibody/immune-mediated/inflammatory response in the
human host organism. In the present invention the terms
"xenoantigen", "antigen", "xenogeneic antigen", "epitope"
and "crucial antigen" can have the same meaning, and can
be used together or to substitute for each other.

The term "connective tissue" comprises among others:
vessels, cardiac valves, tendons, ligaments, pericardium,
muscular fasciae, dura mater, tympanic membrane, intesti-
nal submucosa, cartilage, adipose tissue and bone tissue.

The term "fixed" tissues comprises tissues subjected to
the action of chemical or biological agents such as for the
purposes of non-limiting example: glutaraldehyde, formal-
dehyde and quercitin.

The term "fixed" tissues comprises tissues that, subjected
to the action of chemical or biological agents, develop
intra-tissue cross-links with the function of stabilizing pro-
tein, lipid and cell structures as well as lowering the poten-
tial antigenic action of the host. In the description of the
present invention, the terms "fixed" and "cross-linked" can
describe a same type of treatment and/or have the same
meaning and can be used together or to substitute for each
other.

The term "heterologous" tissues means tissues of non-
human origin. Such tissues can be presented for clinical use
as native or non-treated, instead of being subjected to
treatments that boost their regenerative properties (such as,
for the purposes of purely illustrative example, decellular-
izing procedures or procedures for coating/absorption of
pro-regenerative/preservative substances for the cell com-
ponent). In the description of the invention, the term "het-
erologous" can have the same meaning as "xenogeneic", and
they can be used together or to substitute for each other.

The term "homologous" tissues means tissues of human
origin. Such tissues can be presented for clinical use as
native or non-treated, instead of being subjected to preser-
vative treatments (such as, for the purposes of purely illus-
trative example, cryopreservation) or treatments that boost
their regenerative properties (such as, for the purposes of
purely illustrative example, decellularizing procedures or
procedures for coating/absorption of pro-regenerative/pre-
servative substances for the cell component).

The term "decellularizing procedures" means all indi-
vidual or multiple treatments that use, as non-limiting
examples, saline solutions (hyper-, iso- or hypo-tonic),
detergent solutions (ionic, non-ionic or zwitterionic) and
enzymes, and the purpose of which is the partial, selective
or total removal of the cell component present in the original
tissue.

5

The term "bioprosthetic substitutes" identifies biological devices that are adapted to substitute a missing part of the organism (a limb, an organ or a tissue) or to integrate a damaged part, intended for human or veterinary clinical use. In the description of the present invention, the terms "bio- prosthetic substitutes", "bioprostheses", "biological prosthe- ses" or "device" can have the same meaning, and can be used together or to substitute for each other.

The term "knockout animal for the alpha-Gal antigen" means an animal in which the gene that encodes for the alpha-galactosyltransferase enzyme has been silenced. Such enzyme is responsible for attacking the membrane glyco- proteins and lipoproteins of the alpha-Gal epitope. Its absence causes the production of tissues that completely lack the epitope in question and which in this respect are entirely comparable to the tissue of the human body. In the present invention, knockout animal vascular tissues for the alpha-Gal antigen have been used as an absolute negative control.

Below are some non-limiting examples of application of the method according to the invention.

A method for inactivating xenoantigens in biological tissues according to the invention, particularly for tissues that can be used to manufacture bioprosthetic substitutes and/or in bioprosthetic substitutes that are already prepared and intended for human or veterinary clinical use, comprises the following steps:

providing a solution based on phenolic compounds, poly- phenolic compounds or derivatives thereof, for the inactivation of at least part of the xenogeneic epitopes from such tissues;

incubating the samples to be treated in the various solu- tions based on phenols/polyphenols in controlled con- ditions;

subjecting the treated tissues to a series of washes.

The method also comprises a subsequent procedure of assessing the effective inactivation of the alpha-Gal epitope by way of comparison of treated/untreated tissues and knockout porcine tissues for the gene of the alpha-galacto- syltransferase enzyme.

Such a procedure can be provided for example as dis- closed in Italian patent no. 0001409783 and in EP2626701.

The biological tissues are constituted by connective tis- sues which can be native, or native and fixed, or fixed.

The biological tissues can be heterologous or homolo- gous.

The antigenic epitope is constituted by alpha-Gal antigen.

The controlled conditions of the incubation step comprise at least one treatment at the temperature of $40\pm2°$ C.

The phenolic compounds, polyphenolic compounds or derivatives thereof for the inactivation of at least part of the xenogeneic epitopes from such tissues are constituted by derivatives of cinnamic acid, tannin and oleuropein.

In particular, and by way of example, the cinnamic acid derivatives are constituted by caffeic acid.

In particular, and by way of example, the tannin deriva- tives are constituted by tannic acid.

In particular, and by way of example, the oleuropein derivatives are constituted by hydroxytyrosol.

In particular, and by way of example, at least one phenyl derivative of cinnamic acid is constituted by caffeic acid.

In particular, and by way of example, at least one phenyl derivative of tannin is constituted by tannic acid.

In particular, and by way of example, at least one phenyl derivative of oleuropein is constituted by hydroxytyrosol.

A method for inactivating xenoantigens in biological tissues according to the invention, meaning tissues that can be used to manufacture bioprosthetic substitutes, is applied, by way of non-limiting example of the invention, to the inactivation of the alpha-Gal epitope in tissues constituting the following models of bioprosthetic substitutes:

Hancock II™ Porcine Heart Valve (mod. T510, Medtronic Inc., Minneapolis, USA) indicated in the figures as 'HANCK';

Freestyle® Aortic Root Heart Valve (mod. 995, Medtronic Inc., Minneapolis, USA) indicated in the figures as 'FREE';

Carpentier-Edwards S.A.V.™ (mod. 6650, Edwards Life- sciences LCC, California, USA) indicated in the figures as 'SAV';

Carpentier-Edwards Perimount Plus™ (mod. 6900P, Edwards Lifesciences LCC, California, USA) indicated in the figures as 'PERI';

CardioCel® Cardiovascular Patch (mod. C0404, Adme- dus Regen Pty Ltd, Perth, Australia) indicated in figures as 'CC'.

The method for inactivating xenoantigens in biological tissues, and particularly for inactivating alpha-Gal epitopes in bioprosthetic substitute samples, is described below in the details of an embodiment.

Tissue samples are taken from the bioprosthetic substi- tutes as per the above mentioned models currently available on the market. Such samples are weighed damp after light filter paper blotting (range 30-50 mg) and cut into small pieces in order to increase its exposure surface.

For each bioprosthetic substitute, 4 different sets of samples are prepared (n=8 for each set).

Each set will be subjected to a different method.

4 different solutions are prepared based on phenolic derivatives, corresponding to 4 different applicative variants of the method according to the invention, to which the samples will be subjected in a final volume of 5 ml, specifically:

method T1: caffeic acid at a concentration comprised between 5 mM and 50 mM (in the invention the 20 mM concentration was adopted)/buffer of sodium phosphate with $600\pm50$ U/ml of Tyrosinase in a ratio of [1:20];

method T2: caffeic acid at a concentration comprised between 5 mM and 50 mM (in the invention the 20 mM concentration was adopted) in $0.2\pm0.1M$ of NaOH;

method T3: tannic acid at a concentration comprised between 0.1M and 1.5M (in the invention the 1M concentration was adopted) in a sodium phosphate buffer;

method T4: hydroxytyrosol at a concentration comprised between 0.3 mM and 10 mM (in the invention the 6 mM concentration was adopted) in $0.2\pm0.1M$ of NaOH.

These solutions are left to act under moderate but constant stirring for a total of $12\pm2$ hours at the temperature of $40\pm2°$ C.

At the end of the incubation, the samples are subjected to two washes with isotonic solution, of 15 minutes duration each, and a third washing in a dedicated buffer (TP) of 15 minutes duration.

The assessment of the presence of any epitopes still active on the surface of the treated samples is based on a modifi- cation of the illustrated method by the inventors and described in Italian patent no. 0001409783 and in EP2626701.

Briefly, the treated and washed tissue samples are placed in test tubes to which TP buffer is added up to a final volume comprised between 1000 uL and 1500 uL.

Then a monoclonal mouse antibody, directed against the alpha-Gal epitope, is added (in the present example this is an IgM clone called M86), at the preferable concentration of [1:50] v/v and the whole is incubated for 120±10 minutes at 37±2° C. under constant but moderate stirring.

At the end the samples are subjected to centrifugation at 14,750×g for 30±5 minutes at ambient temperature.

During the incubation with the M86 antibody, a 96-well plate is prepared, in which the bottom of the wells is lined with 100 uL per cell of alpha-Gal/serum albumin at 5 ug/ml in phosphate buffer. The plate thus prepared is incubated for 60±10 minutes at a temperature comprised between 30° C. and 40° C., although it is preferable to stabilize everything at 37° C. Then 3 washes are performed with 300 uL per well of phosphate buffer at ambient temperature.

The first washing is left to act for 5 minutes, the two subsequent washes for 3 minutes.

The blocking is done with 300 uL per well of serum albumin, followed by incubation for 60±10 minutes at ambient temperature, in darkness. Subsequently 3 washes as above are performed.

For each individual well, 100 uL of supernatant, taken after centrifugation from each treated sample, are added.

The samples are loaded into the plate, each type of sample occupying the wells of an entire column. There follows incubation of the plate for 120±10 minutes at a temperature comprised between 30° C.-40° C., although it is preferable to stabilize everything at 37° C.

Then 3 washes as above are performed and 100 uL per well is added of a solution of secondary antibody (rabbit polyclonal anti-mouse) conjugated with peroxidase enzyme (the ideal solutions of such antibody have been found to be [1:1000], [1:500] and [1:100], preferably the intermediate one [1:500] was adopted).

The plate is then incubated again for 60±10 minutes at a temperature comprised between 30° C.-40° C., although it is preferable to stabilize everything at 37° C.

Then 3 washes as above are performed. 100 uL is added per well of a development solution for the peroxidase enzyme, followed by incubation of the plate for 5±1 minutes in darkness.

Subsequently 50 uL is added per well of a stop solution constituted by H2SO4 2M, and the plate is then read in a plate reader at 450 nm.

The percentage inactivation of the epitope in question can be determined by way of comparison between the number of epitopes obtained: in a control tissue constituted by vascular tissue of knockout animals for the alpha-Gal antigen, in untreated bioprosthetic tissues and in the tissues subjected to the various treatments as described above.

It is clear from FIG. 1 that the method in its variation of application T1 displays a marked variability of effect according to the various different bioprosthetic tissues treated.

The T1 method has shown a markedly lower efficacy than the other protocols studied, showing as its best result an inactivation limited to about 43% of the epitopes.

Figure 2:
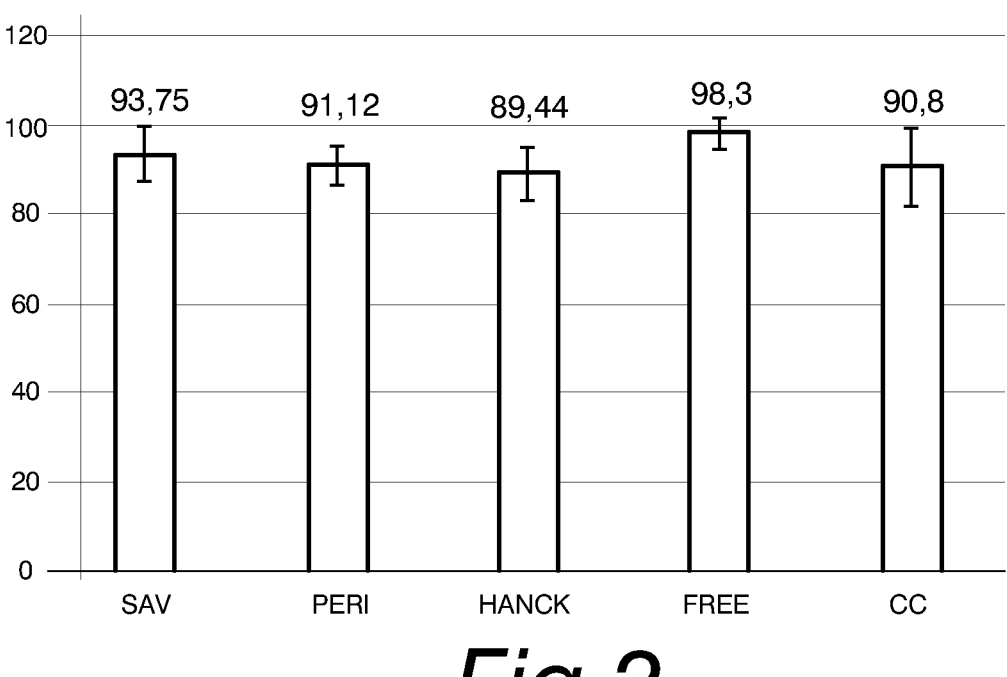
FIG. 2 is a view of the results, in percentages, of the
application of a method according to the invention in a
second variation thereof.
Figures 3, 4:
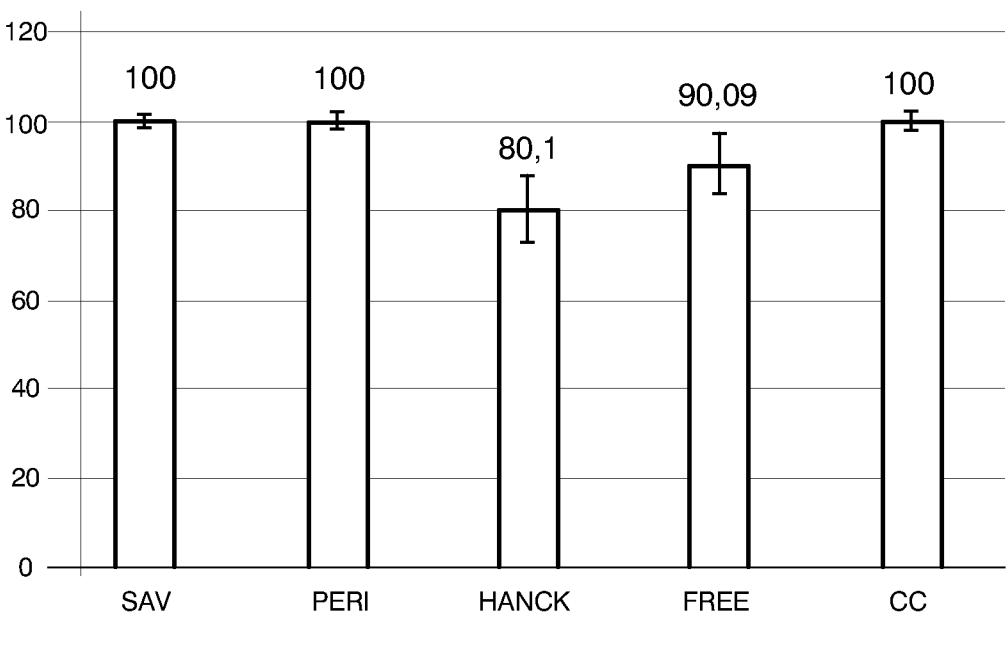
FIG. 3 is a view of the results, in percentages, of the
application of a method according to the invention in a third
variation thereof.
FIG. 4 is a view of the results, in percentages, of the
application of a method according to the invention in a
fourth variation of application thereof.

In FIG. 2 it can be seen that the method in its variation of application T2 with cinnamic acid derivatives only displays an excellent inactivating action against the antigen, with inactivation percentages comprised between 90% and 98%, similarly to the result shown by the method in the T3 variation (FIG. 3, inactivation percentages comprised between 80% and 100%) and T4 variation (FIG. 4, inactivation percentages comprised between 89% and 95%).

The invention also relates to a connective tissue obtained with a method as described above.

Such connective tissue is characterized in that it has at least some of the antigen component in inactive form.

The invention also relates to a use of the connective tissue as described above, for the manufacture of bioprosthetic substitutes and/or parts of bioprosthetic substitutes that are already prepared, for use in the human or veterinary clinical field.

The invention also relates to a kit for carrying out a method for inactivating xenoantigens in biological tissues as described above.

Such kit comprises at least:

one or more containers containing the buffer in which the most suitable dose of phenolic compounds, polyphenolic compounds or derivatives thereof is to be dissolved;

one or more containers containing the dose of phenolic compounds, polyphenolic compounds or derivatives thereof in powder form to be combined with the buffer;

one or more containers containing the washing buffers;

an instruction booklet containing the description of the timings and modes of application of the procedure.

The envisaged use of the kit is aimed at the autonomous treatment of bioprosthetic substitutes that are already prepared, with a method according to the invention as described above, useful for health facilities such as clinics and hospitals.

In practice it has been found that the invention fully achieves the intended aim and objects.

In particular, with the invention a method has been devised for inactivating xenoantigens in biological tissues, and in particular of the alpha-Gal epitope in tissues intended for the production of bioprosthetic substitutes for clinical and/or veterinary use.

Furthermore, with the invention a method has been devised for inactivating the above mentioned antigens, thus ensuring an effective treatment that can be applied to the various different types of tissue bioprostheses currently on the market.

Therefore, with the invention a method has been devised that is potentially capable of not causing, after an implant of a tissue treated with such method, an increase in the anti-alpha-Gal antibodies circulating.

Moreover, with the invention a method has been devised that is capable of limiting the deposition of calcium salts, therefore not favoring the formation of episodes of calcific dystrophy of the valve.

Last but not least, with the invention a method has been devised that can be carried out with conventional devices and machines.

The invention, thus conceived, is susceptible of numerous modifications and variations, all of which are within the scope of the appended claims. Moreover, all the details may be substituted by other, technically equivalent elements.

In practice the components and the materials employed, provided they are compatible with the specific use, and the contingent dimensions and shapes, may be any according to requirements and to the state of the art.

The disclosures in Italian Patent Application No. 102015000078236 (UB2015A006019) from which this application claims priority are incorporated herein by reference.

REFERENCES

Nkomo V T et al. Burden of valvular heart diseases: a population-based study. Lancet 2006; 368:1005-1011.

Zeng L Y et al. A prompt method to quantitative assay of alpha-Gal on pig cell surface without injury. Sichuan Da XUe Xue Bao Yi Xue Ban. 2005; 36(3):419-421.

Galili U et al. A sensitive assay for measuring alpha Gal epitope expression on cells by a monoclonal anti-Gal antibody. Transplantation 1998; 65:1129-1132.

Chen R H et al. alpha-Gal and beta-Gal are preferentially expressed on porcine cardiac microvascular endothelium. Transplant Proc 2000; 32:877-878.

Feng W et al. Distribution of the Alpha-Gal epitope on adult porcine bone tissue. Transplant. Proceed. 2006; 38:2247-2251.

Galili U. The alpha Gal epitope and the anti-Gal antibody in xenotransplantation and in cancer immunotherapy. Immun Cell Biol 2005; 83:674-686.

Konakci K Z et al. Alpha-Gal on bioprostheses: xenograft immune response in cardiac surgery. Eur J Clin Invest 2005; 35(1):17-23.

Park C S et al. Anti alpha-gal immune response following porcine bioprosthesis implantation in children. J Heart Valve Dis 2010; 19(1):124-30.

Lila N et al. Gal knockout pig pericardium: new source of material for heart valve bioprostheses. J Heart Lung Transplant 2010; 29(5):538-43.

Naso F et al. First quantitative assay of alpha-Gal in soft tissues: presence and distribution of the epitope before and after cell removal from xenogeneic heart valves. Acta Biomater 2011; 7(4):1728-1734.

Naso F et al. First quantification of alpha-Gal epitope in current glutaraldehyde-fixed heart valve bioprostheses. Xenotransplantation 2013; 20(4):252-261.

The invention claimed is:

1. A method for inactivating galactose-alpha 1,3-galactose (alpha-Gal) xenoantigen by binding to at least a part of a xenogeneic epitope of alpha-Gal in xenogeneic biological tissues adapted for manufacture of bioprosthetic substitutes and/or in bioprosthetic substitutes comprising said xenogeneic biological tissues that are already prepared and for implantation in humans, comprising the following steps:

providing a solution comprising caffeic acid, for binding to at least part of the alpha-Gal xenogeneic epitope of said xenogeneic biological tissues;

incubating the xenogeneic biological tissues adapted for manufacture of the bioprosthetic substitutes and/or in bioprosthetic substitutes in the solution comprising caffeic acid in controlled conditions, wherein the solution comprising caffeic acid inactivates the xenogeneic epitope of alpha-Gal; and subjecting the xenogeneic biological tissues to a series of washes;

wherein the xenogeneic biological tissues are not subjected to decellularizing procedures;

wherein after implantation of a bioprosthetic substitute comprising the treated xenogeneic biological tissue, circulating anti-alpha-Gal antibodies do not increase in response to the implantation of the treated xenogeneic biological tissue.

2. The method according to claim 1, wherein said xenogeneic biological tissues comprise native, or native and fixed, or fixed connective tissues.

3. The method according to claim 1, wherein said controlled conditions comprise at least treatment at the temperature of $40 \pm 2°$ C.

4. The method according to claim 1, further comprising detecting the inactivation of the alpha-Gal epitope.

5. The method according to claim 1, wherein the series of washes includes a first set of washes and a second set of washes.

6. The method according to claim 5, wherein the first set of washes comprises an isotonic solution.

7. A method for inactivating galactose-alpha 1,3-galactose (alpha-Gal) xenoantigen by binding to at least a part of a xenogeneic epitope of alpha-Gal in xenogeneic biological tissues adapted for manufacture of bioprosthetic substitutes and/or in bioprosthetic substitutes comprising the xenogeneic biological tissues that are already prepared and for implantation in humans, comprising the following steps:

providing a solution comprising a concentration of caffeic acid between 5 mM and 50 mM, for binding to at least part of the alpha-Gal xenogeneic epitope of said xenogeneic biological tissues;

incubating the xenogeneic biological tissues adapted for manufacture of the bioprosthetic substitutes and/or in bioprosthetic substitutes in the solution comprising caffeic acid in controlled conditions, wherein the solution comprising caffeic acid inactivates the xenogeneic epitope of alpha-Gal; and subjecting the xenogeneic biological tissues to a series of washes, wherein the xenogeneic biological tissues are not subjected to decellularizing procedures, wherein the treated xenogeneic biological tissue comprises a percentage inactivation of the xenogeneic epitope of alpha-Gal.

* * * * *